United States Patent

Shoher et al.

Patent Number: 5,272,184
Date of Patent: Dec. 21, 1993

[54] METAL COMPOSITE AND METHOD FOR FILLING A DENTAL CAVITY IN THE PREPARATION OF A DENTAL RESTORATION

[76] Inventors: Itzhak Shoher, 50 Shlomo-Hamelech St., Tel Aviv, Israel, 64386; Aharon E. Whiteman, J. L. Perez St., Petach-Tikva, Israel, 49206

[21] Appl. No.: 951,767

[22] Filed: Sep. 28, 1992

[51] Int. Cl.⁵ .......................... C08L 3/00; A61C 5/00
[52] U.S. Cl. .................. 523/118; 433/228.1; 433/226; 433/227; 433/222.1
[58] Field of Search ............... 523/116; 433/226, 227, 433/228.1, 222.1

[56] References Cited

U.S. PATENT DOCUMENTS

| 4,355,980 | 10/1982 | Dwight | 433/226 |
| 4,742,861 | 4/1988 | Shoher et al. | 164/80 |
| 4,814,008 | 3/1989 | Shoher et al. | 75/252 |
| 4,990,394 | 2/1991 | Shoher et al. | 428/212 |
| 4,997,699 | 3/1991 | Shoher et al. | 428/212 |

Primary Examiner—Paul R. Michl
Assistant Examiner—LaVonda DeWitt
Attorney, Agent, or Firm—Eugene Lieberstein

[57] ABSTRACT

A metal composite and method for filling a dental cavity independent of cavity size. The dental metal composite comprises high-fusing temperature particles, low-fusing temperature particles, and a wax binder, and is inserted into the cavity to replicate the cavity, removed for heat treatment, densified, and reinserted to complete the filling operation.

12 Claims, 1 Drawing Sheet

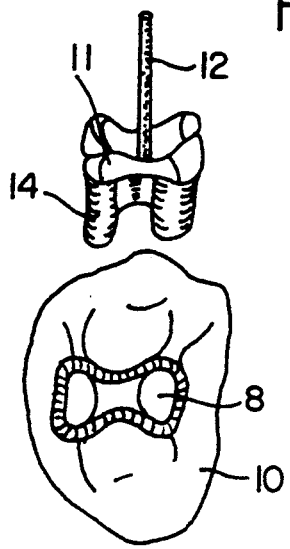
FIG. 1
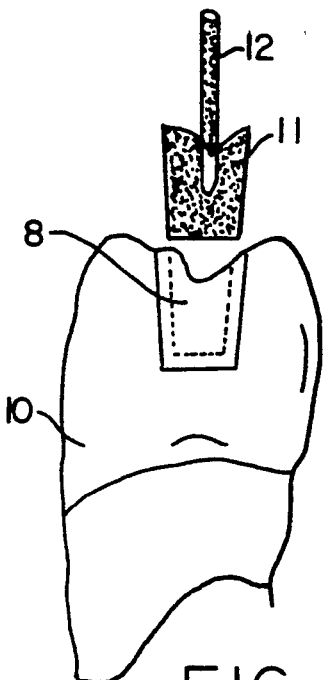
FIG. 2
FIG. 4
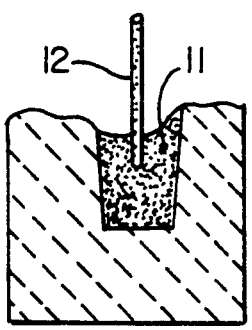
FIG. 3
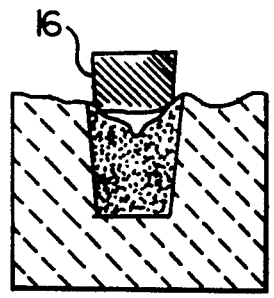
FIG. 5
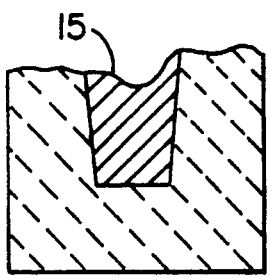
FIG. 6

METAL COMPOSITE AND METHOD FOR FILLING A DENTAL CAVITY IN THE PREPARATION OF A DENTAL RESTORATION

FIELD OF THE INVENTION

This invention relates to a metal composite and method for filling a dental cavity in the preparation of a dental restoration.

BACKGROUND OF THE INVENTION

Historically, a cavity in a vital tooth has been filled using either a gold filling or an amalgam of silver and mercury. Concern over the potential health hazard from the use of mercury in dental fillings has created a need for a substitute dental filling material and/or method for filling teeth using a filling material which does not contain mercury. Ceramic materials and composites have been investigated and are, to a limited extent, currently used as a substitute for the mercury amalgam. The ceramic materials do not, however, form as durable or as strong a filling in comparison to a mercury amalgam or a gold-based metal filling. For larger cavities, an inlay, partial veneer or full veneer is usually indicated, and is almost exclusively fabricated with metal. At present, the inlay preparation requires laboratory involvement similar to the effort and expense in making a full crown.

The procedure currently practiced for preparing an inlay, onlay, or veneer requires careful cavity preparation, followed by taking an impression of the cavity which is then forwarded to a dental laboratory to prepare a casting in much the same manner as in the preparation of a full crown. The inlay or onlay may also result in an unsightly exhibition of metal since it is difficult to form a coating of porcelain for application to only a specific area or surface. Moreover, the inlay may fit poorly if the casting does not accurately reproduce the anatomical contour of the cavity.

SUMMARY OF THE INVENTION

A metal composite has been discovered in accordance with the present invention suitable as a substitute for the mercury amalgam in filling a dental cavity, and preferably in accordance with a novel direct-indirect filling technique, which permits the metal composite to be used as a universal filling material for small or large cavities, including the preparation of inlays, onlays, or a veneer. The metal composite of the present invention is, preferably, inserted directly into the dental cavity to form a replica of the anatomical contour of the cavity. Upon removal from the cavity, the composite is heat treated to form a porous metal sponge which is then filled with a filler material to form a solid structure having the shape of the dental cavity, and reinserted into the dental cavity to complete the filling operation.

Broadly, the method of the present invention is a direct-indirect technique for filling a dental cavity in a vital or nonvital tooth within the mouth of a dental patient, comprising the steps of:

forming a metal composite comprising particles of a high-fusing temperature metal, particles of a low-fusing temperature metal, and a binder substantially of wax in a concentration of at least about thirty percent (30%) by volume of said composite;

inserting the metal composite in situ, into the dental cavity;

compacting the composite in the cavity to form a shaped composite conforming to the anatomical contour of the cavity;

removing the shaped composite from the cavity;

heat treating the shaped composite material at a temperature below the melting temperature of the high-fusing temperature metal particles, to volatize said wax and to form a porous metal sponge having a void volume of above at least thirty percent (30%);

adding a filler material into the porous metal sponge to fill the voids for forming a solidified structure; and cementing the solidified structure into the dental cavity to complete the filling operation.

The present invention also relates to a metal composite for use as a dental kit in filling a dental cavity, comprising a first dental material composed of particles of a high-fusing temperature metal, particles of a low-fusing temperature metal, and a binder substantially of wax in a concentration of at least about thirty percent (30%) by volume of said dental material, and a second material having a melting temperature below the melting temperature of the high-fusing temperature metal particles and selected from the group consisting of precious metals, ceramics, and plastics, for filling the voids in said first dental material formed upon heat treatment at a temperature substantially equal to the melting temperature of the low-fusing particles. The binder should, preferably, be nonaqueous and nonliquid, and may include additives selected from the group consisting of an elastomer, self-hardening plastic material and a photopolymerizable material responsive to light energy.

BRIEF DESCRIPTION OF THE DIAGRAMS

Other objects and advantages of the present invention will become apparent from the following detailed description of the invention when read in conjunction with the accompanying drawings, of which:

FIG. 1 is an exploded view partially in perspective, showing a shaped metal composite removed from a dental cavity of a molar tooth for heat treatment in the preparation of a filling in accordance with the present invention;

FIG. 2 is an end view of FIG. 1;

FIG. 3 shows an embodiment of the rod which may be used for removing the composite from the cavity;

FIG. 4 shows the dental composite of FIG. 1 surrounded by investment material in preparation for solidification following heat treatment;

FIG. 5 is a view similar to FIG. 4, illustrating one embodiment for solidifying heat-treated composite material; and FIG. 6 shows the solidified structure of FIG. 5 in the investment material.

DETAILED DESCRIPTION OF THE INVENTION

The dental material of the present invention comprises a composite of metal particles and a binder substantially of wax, based upon the teaching of Applicants's companion application, Ser. No. 801,028, filed on Dec. 2, 1991 now abandoned, and entitled "Moldable Dental Material and Composite," the disclosure of which is herein incorporated by reference. The dental material, as more fully described in the companion application, comprises a uniform mixture of high-fusing temperature metal particles, low-fusing temperature metal particles, and a binder of wax. The binder, in accordance with the present invention, is preferably formulated from a nonaqueous, nonliquid composition substantially of wax. Additional additives or agents may be added to the wax in formulating the binder to modify the physical characteristics of the composite so that it forms a moldable putty which will replicate the dental cavity upon insertion, and which is capable of removal from the cavity with minimal distortion.

The need for additives, if any, depends upon the complexity of the cavity geometry and the extent to which distortion is acceptable. However, for most typical dental filling operations, a binder, primarily or solely, of wax should be adequate. The additives are intended to render the binder more elastic, with the option of increasing hardness after insertion into the cavity. Elasticity may be increased by using an additive such as an elastomer, a synthetic rubber, gum, or polysaccharide and, preferably, an additive selected from the group consisting of a butadiene or isoprene polymer, phenol formaldehyde, polychloroprene, and magnesium resinate. Other or alternative additives may also be included to increase the material hardness at room temperature, or by the application of light energy from a visible or ultraviolet light. Well known photopolymerizable materials include dimethacrylate and diacrylate resins which respond to ultraviolet light, and urethanes formed from acrylated polyesters, such as bis-GMA, which, in conjunction with a photoinitiator, responds to visible light. Alternatively, a room temperature self-hardening plastic composition may be used.

If an additive such as a light-activated material is added to the binder, the binder should be exposed to light to cure the material. Self-hardening additives may be used to promote and accelerate a relative hardening of the binder, to facilitate removal of the composite from the cavity. The shaped composite should have enough elasticity to overcome small undercuts in the cavity. The additives should represent no more than fifty percent (50%) of the total content of the binder.

It is also within the scope of the present invention to apply the hardening photopolymerizable composition to the occlusal surface of the filled cavity, i.e., over the composite to form a coating or surface layer which will selectivity harden the occlusal surface of the composite before removal.

The concentration of the binder should represent at least about thirty percent (30%) by volume of the composite material, and up to seventy-five percent (75%). The wax in the binder permits the composite to be heat treated to form a porous metal sponge of interconnected high-fusing temperature metal particles with a substantial network of voids uniformly distributed throughout the sponge-like structure, having a void volume of at least thirty percent (30%) after heat treatment. The wax composition may be selected from natural wax, mineral wax, organic wax, or a synthetic wax composition. The wax composition should be relatively soft and tacky, and should melt relatively cleanly without leaving a significant residue. The melting temperature of the wax must be below the melting temperature of the low-fusing temperature metal particles. Moreover, the high- and low-fusing temperature metal particles should combine readily with the wax at room temperature to form a mixture with a uniform distribution of metal particles in the wax. Alternatively, the wax can be heated and the particles added and mixed, to form a uniform distribution of metal particles.

The high-fusing temperature metal component of the composite may be of a single metal or metal alloy, preferably of precious metals such as platinum and palladium, in any desired proportion relative to each other, with or without other constituents such as gold, silver, copper, magnesium, aluminum, zinc, gallium, indium, and other metals or elements from the third, fourth, or fifth group of elements of the periodic table. Gold may be added to the high-fusing temperature metal component to increase the affinity between the high-fusing temperature metal particles and the low-fusing temperature metal particles. The shape of the high-fusing temperature metal particles in the composite is very important to the formation of the porous structure upon heat treatment. At least a majority, and preferably all, of the high-fusing particles should be irregular in shape and, particularly in the shape of flake-like platelets. A spherical shape should be avoided.

The particles of low-fusing temperature metal are composed preferably of gold or a gold alloy, with gold as the major constituent. The preference for gold as the major constituent of the low-fusing component is based on its known characteristics of workability, biocompatibility, non-oxidizing properties, and color. The particles of high- and low-fusing temperature metal should be selected with an average particle size of between 2 to 80 microns, and preferably between 4 to 32 microns. The size of the particles of high-fusing temperature metal may vary in range from a size equal to the size of the low-fusing particles to a size of up to ten times the size of the low-fusing metal particles. The volume relationship of the metals in the composite mixture should be in a range of from about fifteen (15%) to seventy-five percent (75%) of the low-fusing component relative to the high-fusing component, and preferably from thirty (30%) to sixty-five percent (65%). The composition of the selected metal particles for the high- and low-fusing components will determine the optimum volume ratio. The weight ratio will vary with the specific gravity of the selected materials, as evidenced by the examples at the end of the specification.

The cavity (8), as shown in FIG. 1, may be formed in a single tooth (10) or may extend from or between one or more tooth surfaces, such as the occlusal, mesial, distal, buccal, or lingual surfaces of several teeth. Because of the high concentration of wax in the composite, it has a putty-like texture and will readily assume the geometry of the cavity (8) with minimal pressure. The shaped composite (11) is then removed from the cavity (8) by pulling it out with an instrument or by inserting a member (12), in the form of a rod, into the composite (11), as shown in FIGS. 1 and 2, to facilitate lifting the composite (11) from the cavity (8) of the tooth (10) without causing significant deformation. The rod-like member (12) may be of a metal or plastic composition, and may be solid or hollow. The rod-like member (12) may have any desired cross-sectional geometry, such as cylindrical or rectangular, and may be "U-shaped." The member (12) may also be formed with a hook or bend at one end (not shown), to assist in the removal of the composite. Alternatively, the embedded section of the member (12) may have a protruding shoulder (13) of conical geometry, such as a chamfered flange, as shown in FIG. 3, to facilitate removal of the shaped composite (11).

Upon removal from the dental cavity, the shaped composite (11) is heat treated to form a porous metal structure having a void volume between thirty percent (30%) and eighty percent (80%). The size of the metal particles, their ratio, and predominantly, the concentration of binder in the mixture of high- and low-fusing temperature metal particles will control the void volume of the porous structure formed by heat treatment. A capillary network interconnecting the voids is also formed in the porous mass, which controls the absorption and accommodation of the added filler material to fill the voids after heat treatment. The heat treatment must eliminate the wax in the binder, preferably without leaving a residue, and must be high enough in temperature to cause the low-fusing particles to melt without melting the high-fusing particles.

The shaped composite (11) may be embedded in a conventional refractory investment material, as shown in FIG. 4, during or before heat treatment, or may be heat treated as a free-standing body and surrounded by a refractory investment following heat treatment. Heat treating the dental composite in investment material simplifies filling the voids in the porous structure following heat treatment. If heat treated as a free-standing body, it is preferred to cover the surfaces which interface with the cavity walls with an antiflux following heat treatment, as will be discussed hereafter. The heat treatment may itself occur in a furnace, over a flame, or by the application of a high frequency source of energy, etc., provided it substantially eliminates the binder and substantially melts the low-fusing temperature metal particles to produce a porous sponge having a high void volume, as heretofore explained. The heat treatment temperature is between 800° C. and 1200° C.

After heat treatment, a filler material is melted into the voids of the heat-treated porous structure to solidify the structure before reinsertion into the dental cavity. The porous metal structure may be reshaped, if desired, to assure a proper fit in forming the final dental restoration, before the filler material is added. The filler material may be any suitable ceramic, polymeric, or metal composition, preferably a gold-based precious metal composition. The filler material may also be in the form of a matrix of particles of filler material, and may be mixed with a wax component to form a wax body, which is placed over the porous structure, as shown in FIG. 5, to simplify the filling operation pursuant to a second heat treatment at a suitable temperature below the melting temperature of the high-fusing metal particles. For a filler material of metal or of metal alloy, the second heat treatment temperature may be substantially equal to or above the first heat treatment temperature. The second heat treatment causes the filler metal to melt into the porous sponge to fill the voids. It should be noted that the first heat treatment forms metal joints connecting the high-fusing temperature particles together. The joints are formed of an alloy of high- and low-fusing metals, i.e., due to diffusion and migration from the high-fusing particles, which has a melting temperature above the low-fusing metal melting temperature. Accordingly, the second heat treatment will not melt the joints, even if it is equal to the first heat-treatment temperature. Once the porous structure is filled and solidified, it is recovered from the investment, cleaned, and, if desired, polished. The filler material may be in any particulate form, as a solid, a gel, or a liquid. If the filler is a liquid or is liquified, a hollow member (12) may be used to introduce the filler material into the porous sponge.

The member (12), which aids in the removal of the composite from the dental cavity, may also function as the filler metal during the second heat treatment. In this instance, the member (12) should melt during the second heat treatment, but at a temperature higher than the first heat-treatment temperature, so that the porous sponge structure is permitted to form before the temperature is elevated to the second heat-treatment temperature to melt the filler metal. The melting temperature of the filler metal must also be lower than the melting temperature of the high-fusing temperature metal particles. Thus, if the porous sponge structure is formed at 1000° C., the filler metal may have a melting temperature of, for example, between 1050° C. and 1150° C.

As earlier stated, the heat treatment of the metal and wax dental composite after removal from the dental cavity may occur in investment material, as shown in FIG. 4, or with the dental composite as a free-standing body. If heat treated as a free-standing body, the metal porous sponge structure may then be densified in investment as a free-standing body or submerged into a bath of molten filler metal. It is important that the voids of the porous metal structure be filled to form a solidified body without changing the exterior dimensions of the heat-treated composite structure (11), particularly on the surfaces (14) where it interfaces with the cavity walls. Otherwise, it will no longer have the shape of the cavity (8) into which it is being reinserted to complete the filling. This may be prevented by covering the free-standing composite (11) with a protective layer of antiflux. A suitable antiflux material may be a ceramic or glass composition, or even graphite. A preferred alternative is to use a premeasured amount of filler metal relative to the weight of the metal in the composite (11), so that no excess material will exude out from the surface of the free-standing porous body during the second heat treatment. Once the amount is determined for a given predetermined weight of metal composite, which can be ascertained by trial and error or by experimentation, it may be standardized for that weight, i.e., for a standard tooth size. A different amount will be required if the filler metal composition is changed or for other filler materials, such as a ceramic or polymeric material, and, of course, for other predetermined metal composite weights. The different metal composite weights can correspond to different size restorations or fillings. The solidified composite structure (15), as shown in FIG. 6, is identical in shape to the shaped composite (11). The solidified composite structure (15) is then removed from the investment and reinserted into the cavity using any conventional dental cement.

What we claim is:

1. A direct-indirect method for filling a dental cavity in a vital or nonvital tooth within the mouth of a dental patient, comprising the steps of:

forming a metal composite comprising particles of a high-fusing temperature metal, particles of a low-fusing temperature metal, and a binder substantially of wax in a concentration of at least thirty percent (30%) by volume of said composite;

inserting the metal composite in situ, into the dental cavity;

compacting the composite in the cavity to form a shaped composite conforming to the anatomical contour of the cavity;

removing the shaped composite from the cavity;

heat treating the shaped composite at a temperature below the melting temperature of the high-fusing temperature metal particles, to volatize said wax and to form a porous metal sponge having a void volume of above at least thirty percent (30%);

adding a filler material into the porous metal sponge to fill the voids for forming a solidified structure; and cementing the solidified structure into the dental cavity to complete the filling operation.

2. A direct-indirect method, as defined in claim 1, further comprising inserting a member into said composite to facilitate its removal from the cavity.

3. A direct-indirect method, as defined in claim 2, wherein said member is composed of metal.

4. A direct-indirect method, as defined in claim 3, wherein said metal member has a protruding shoulder to facilitate removal of the shaped composite from the cavity.

5. A direct-indirect method, as defined in claim 2, wherein said binder includes additives selected from the group consisting of: elastomer(s), gum(s), synthetic rubber, self-hardening plastic(s) and photopolymerizable materials.

6. A direct-indirect method, as defined in claim 2, wherein a photopolymerizable material is applied to the occlusal surface of said shaped composite to form a hard coating upon application of light energy.

7. A direct-indirect method, as defined in claim 2, wherein said shaped composite is heat treated at a temperature between 800° C. and 1200° C.

8. A direct-indirect method, as defined in claim 7, wherein said shaped composite is heat treated in refractory investment material.

9. A direct-indirect method, as defined in claim 7, wherein said shaped composite is heat treated as a freestanding body.

10. A direct-indirect method, as defined in claim 2, wherein said filler material comprises a material selected from the group consisting of metal, ceramic, or plastic.

11. A dental composite for use as a dental kit in filling a dental cavity, comprising a first dental material composition composed of particles of a high-fusing temperature metal of irregular shape, particles of a low-fusing temperature metal, and a binder composed substantially of wax in a concentration of at least about thirty percent (30%) by volume of said dental composite, and a second material having a melting temperature below the melting temperature of said high-fusing temperature metal particles and selected from the group consisting of precious metals, ceramics, and plastics, for filling the voids in said first dental material formed upon heat treatment at a temperature substantially equal to the melting temperature of said low-fusing temperature metal.

12. A dental composite, as defined in claim 11, wherein said high- and low-fusing temperature metal particles vary in a size range of between 2 to 80 microns.

* * * * *